(12) United States Patent
Kruszewski et al.

(10) Patent No.: US 12,329,515 B2
(45) Date of Patent: Jun. 17, 2025

(54) DERIVING INSIGHTS INTO MOTION OF AN OBJECT THROUGH COMPUTER VISION

(71) Applicant: Hinge Health, Inc., San Francisco, CA (US)

(72) Inventors: Paul Anthony Kruszewski, Westmount (CA); Wenxin Zhang, Verdun (CA); Robert Lacroix, Saint-Lambert (CA); Ryan Russell, Bellevue, WA (US)

(73) Assignee: Hinge Health, Inc., San Francisco, CA (US)

( * ) Notice: Subject to any disclaimer, the term of this patent is extended or adjusted under 35 U.S.C. 154(b) by 665 days.

(21) Appl. No.: 17/520,440

(22) Filed: Nov. 5, 2021

(65) Prior Publication Data

US 2022/0142514 A1 May 12, 2022

Related U.S. Application Data

(60) Provisional application No. 63/110,660, filed on Nov. 6, 2020.

(51) Int. Cl.
| | |
|---|---|
| *A61B 5/11* | (2006.01) |
| *G06T 7/20* | (2017.01) |
| *G06T 7/70* | (2017.01) |
| *G06V 40/20* | (2022.01) |

(52) U.S. Cl.
CPC ............ *A61B 5/1128* (2013.01); *A61B 5/112* (2013.01); *G06T 7/20* (2013.01); *G06T 7/70* (2017.01); *G06V 40/23* (2022.01); *G06T 2207/20084* (2013.01); *G06T 2207/30196* (2013.01)

(58) Field of Classification Search
CPC ........ G06V 10/82; G06V 40/23; G06V 40/25; G06T 7/20; G06T 7/70; G06T 2207/20084; G06T 2207/30004; G06T 2207/30104; G06T 2207/30196; A61B 5/015;
(Continued)

(56) References Cited

U.S. PATENT DOCUMENTS

| | | | |
|---|---|---|---|
| 7,962,898 B1 * | 6/2011 | Petry | G06V 10/95 717/124 |
| 9,566,004 B1 | 2/2017 | Radwin et al. | |
| 10,529,137 B1 * | 1/2020 | Black | G06T 15/04 |

(Continued)

FOREIGN PATENT DOCUMENTS

| | | |
|---|---|---|
| JP | 2017097903 A | 6/2017 |
| JP | 2020077388 A | 5/2020 |

(Continued)

OTHER PUBLICATIONS

Yuan, Meixue, et al. "A systematic survey on human behavior recognition methods." SN Computer Science 3.1, p. 6 (Year: 2022).*

(Continued)

*Primary Examiner* — Scott A Rogers
(74) *Attorney, Agent, or Firm* — Perkins Coie LLP

(57) ABSTRACT

Introduced here are computer programs that are able to generate computer vision data through local analysis of image data (also referred to as "raw data" or "input data"). The image data may be representative of one or more digital images that are generated by an image sensor. Also introduced here are apparatuses for generating and handling the image data and computer vision data.

32 Claims, 12 Drawing Sheets

(58) Field of Classification Search
CPC ......... A61B 5/11; A61B 5/112; A61B 5/1107; A61B 5/1117; A61B 5/1113–1128
See application file for complete search history.

(56) References Cited

U.S. PATENT DOCUMENTS

| | | | | |
|---|---|---|---|---|
| 10,842,415 | B1* | 11/2020 | Jagannathan | A61B 5/112 |
| 11,270,461 | B2* | 3/2022 | Tsang | G06T 7/74 |
| 11,328,534 | B2* | 5/2022 | Mehl | A61B 5/725 |
| 11,918,370 | B2* | 3/2024 | Adeli-Mosabbeb | A61B 5/1124 |
| 11,950,901 | B2* | 4/2024 | Jagannathan | G16H 40/67 |
| 2010/0004784 | A1* | 1/2010 | Chang | H04N 13/10 700/259 |
| 2011/0043630 | A1 | 2/2011 | McClure et al. | |
| 2011/0317907 | A1* | 12/2011 | Petry | G06V 10/95 382/141 |
| 2012/0253201 | A1 | 10/2012 | Reinhold | |
| 2013/0073847 | A1* | 3/2013 | Scherer | H04L 63/0227 713/160 |
| 2017/0007137 | A1 | 1/2017 | Hong et al. | |
| 2017/0296874 | A1 | 10/2017 | Zamir et al. | |
| 2021/0264144 | A1* | 8/2021 | Cho | G06N 3/045 |
| 2022/0331028 | A1* | 10/2022 | Sternitzke | G05D 1/0094 |
| 2022/0392082 | A1* | 12/2022 | Vanderpool | H04N 23/633 |
| 2023/0170069 | A1* | 6/2023 | Groteke | G16H 30/40 382/128 |
| 2024/0095951 | A1* | 3/2024 | Ramachandra | G06N 3/045 |

FOREIGN PATENT DOCUMENTS

| | | |
|---|---|---|
| JP | 2020123239 A | 8/2020 |
| KR | 20190060679 A | 6/2019 |

OTHER PUBLICATIONS

Eklund, Anders, et al. "Medical image processing on the GPU—Past, present and future." Medical image analysis 17(8) pp. 1073-1094 (Year: 2013).*

Fung, James, and Steve Mann. "Computer vision signal processing on graphics processing units." 2004 IEEE International Conference on Acoustics, Speech, and Signal Processing. vol. 5. IEEE (Year: 2004).*

International Search Report and Written Opinion mailed Mar. 21, 2022 for International Patent Application No. PCT/US21/58332, 9 pages.

Ghazisaeidi, "Estimating Human Limb Motion from Video Sequences with Anatomical Knowledge", Ghazisaeidi; In: Ottawa-Carleton Institute for Electrical and Computer Engineering, Jan. 2011, [retrieved on Jan. 5, 2022) from < URL: http://docplayer.neU203000356-Estimating-human-limb-motion-fromvideo-sequences-with-anatomical-knowledge.html/>, Jan. 2011, pp. 7, 8, 13, 85-86.

Mehrizi, et al., "Automatic Health Problem Detection from Gait Videos Using Deep Neural Networks", Mehrizi et al.; In: arXiv.org/cs, [online] Jan. 27, 2020, [retrieved on Jan. 5, 2022 (Jan. 5, 2022)) Retrieved from the Internet< URL: https://arxiv.org/abs/1906.01480 />, 9 pages.

Mehrizi, Rahil, et al., "Automatic Health Problem Detection from Gait Videos Using Deep Neural Networks", arxiv.org, Cornell University Library, 201 Olin Library Cornell University Ithaca, NY 14853, 8 pages.

Viswakumar, Aditya, et al., "Human Gait Analysis Using OpenPose", 2019 Fifth International Conference on Image Information Processing (ICIIP), IEEE, Nov. 15, 2019 (Nov. 15, 2019), pp. 310-314, XP033708152, DOI: 10.1109/ICCIIP47207.2019.8985781 [retrieved on Feb. 6, 2020], 310-314.

* cited by examiner

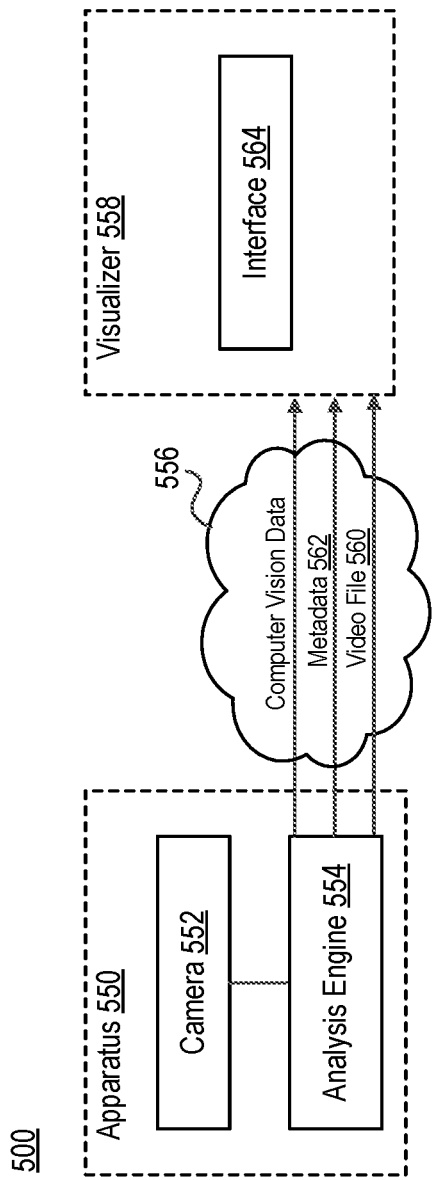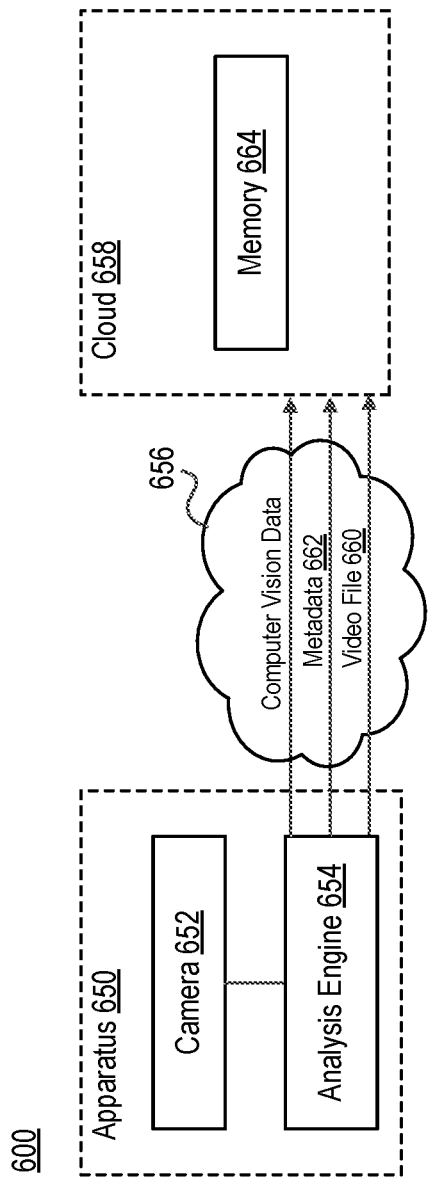

1300

1310
Acquire a series of digital images generated by an image sensor in rapid succession of a physical environment in which a patient is situated 1320
Apply a model to the series of digital images to produce a series of outputs that are collectively representative of computer vision data 1330
Assess, based on the computer vision data, health of the patient in real time 1340
Perform an action based on the health of the patient

FIGURE 13

DERIVING INSIGHTS INTO MOTION OF AN OBJECT THROUGH COMPUTER VISION

CROSS-REFERENCE TO RELATED APPLICATIONS

This application claims priority to U.S. Provisional Application No. 63/110,660, titled "Computer Vision Data" and filed on Nov. 6, 2020, which is incorporated by reference herein in its entirety.

TECHNICAL FIELD

Various embodiments concern computer programs and associated computer-implemented techniques for deriving insights into the motion of an object through analysis of computer vision data, as well as systems and apparatuses capable of generating computer vision data.

BACKGROUND

Computer vision is an interdisciplinary scientific field that deals with how computing devices can gain higher level understanding of the content of digital images. At a high level, computer vision represents an attempt to understand and automate tasks that the human visual system can perform.

Computer vision tasks include different approaches to acquiring, processing, analyzing, and understanding the content of digital images, as well as inferring or extracting data from the real world in order to produce more symbolic information (e.g., decisions). In this context, the term "understanding" refers to the transformation of visual content into non-visual descriptions that "make sense" to computer-implemented processes, and thus can elicit appropriate action. In a sense, this "understanding" can be seen as the disentangling of symbolic information from the digital images through the use of algorithms.

Generally, performance of a computer vision task will involve the application of a computer-implemented model (or simply "model") that is representative of one or more algorithms designed to perform or facilitate the computer vision task. The nature of these algorithms will depend on the intended application of the application. Regardless of application, when applied to one or more digital images, the data that is produced by a model may be referred to as "computer vision data."

Computer vision data may be used in various contexts, including computer-generated imagery in the firm, video game, entertainment, biomechanics, training, and simulation industries. Moreover, computer vision data may be used for real-time control or management of human-machine interfaces.

As an example, consider the process by which animations for films and video games are produced. To create an animation, an individual may need to reserve time in a studio that includes a sophisticated vision capture system that records the individual while the animation is performed. The image data generated by the vision capture system can then be fed into another system (e.g., a computer-implemented animation system) that is responsible for determining how to programmatically recreate the animation.

As another example, consider the process by which locomotion of a human body is visually studied to gain insights into the activity of various muscles. This process is generally referred to as "gait analysis." In order to have her gait analyzed, a patient may need to visit a hospital that includes a sophisticated vision capture system that records the patient while she moves about a physical environment. The image data generated by the vision capture system can then be fed into another system (e.g., a computer-implemented diagnostic system) that is responsible for assessing whether any aspects of the gait are unusual.

As can be seen from these examples, generating computer vision data tends to a laborious and costly process. In addition to requiring sophisticated vision capture systems, the individuals being recorded must visit facilities that include these sophisticated vision capture systems. These drawbacks limit the applications of computer vision.

BRIEF DESCRIPTION OF THE DRAWINGS

FIG. 5 illustrates an example of system in which an apparatus is communicatively connected to another computing device that acts as a visualization system.

FIG. 6 illustrates an example of a system in which an apparatus is communicatively connected to a network-accessible resource (also referred to as a "cloud-based resource" or simply "cloud").

FIG. 13 includes a flowchart of a method for determining the health status of an individual through analysis of computer vision data.

Figures 1, 2:
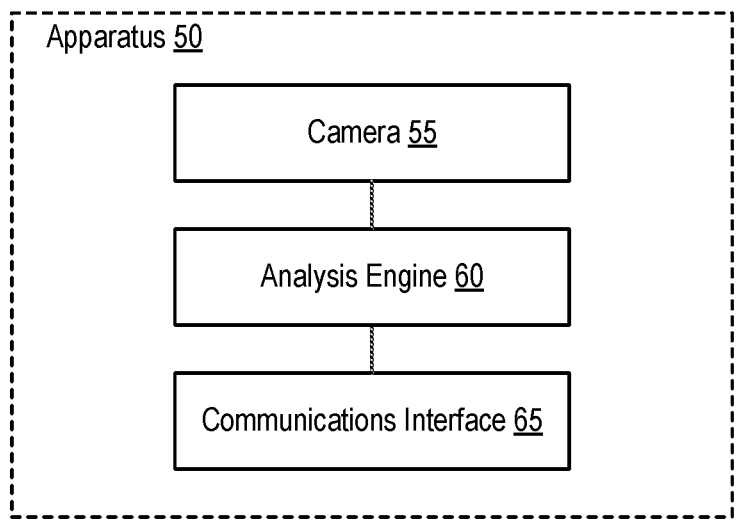
FIG. 1 includes a schematic representation of an apparatus configured to generate computer vision data based on raw data that is captured by the apparatus.
FIG. 2 includes a flowchart of a method for generating computer vision data based on raw data.

Various features of the technology described herein will become more apparent to those skilled in the art from a study of the Detailed Description in conjunction with the drawings. Various embodiments are depicted in the drawings for the purpose of illustration. However, those skilled in the art will recognize that alternative embodiments may be employed without departing from the principles of the technology. Accordingly, although specific embodiments are shown in the drawings, the technology is amenable to various modifications.

DETAILED DESCRIPTION

Computer vision data can be used in a broad range of different sectors to better understand the motion of objects. One example of an object is a human body. Computer vision data typically includes two-dimensional (2D) representations or three-dimensional (3D) representations of each object whose motion is being computed, inferred, or otherwise determined. Since computer vision data is indicative of a higher level representation of motion, it may be used by "downstream" computer programs for various purposes. As examples, computer vision data may be used to generate animations, detect events, and model scenes. The characteristics of computer vision data—in particular, its form and content—may depend on its ultimate application, and therefore are not particularly limited.

Similarly, the generation of computer vision data is not particularly limited. Computer vision data could be manually generated by an individual (also referred to as a "programmer," "operator," or "designer"), or computer vision data could be automatically generated by a computer program based on, for example, an analysis of digital images. As an example, a camera system that includes one or more camera modules (or simply "cameras") may be used to capture digital images of a person from multiple viewpoints. Then, the digital images may be processed by a processor in order to convert these "raw" digital images into computer vision data. Note that the processor could be included in the camera system or a computing device that is communicatively connected to the camera system. The computer vision data may include information such as a 3D skeletal representation of the joints of a person, a 2D skeletal representation of the joints of a person from a particular point of view, data relating to overlapping objects in the digital images, or any combination thereof. These skeletal representations may be referred to as "skeletons" for convenience. The computer vision data can then be used for various purposes.

Historically, the entire system responsible for performing computer vision tasks is designed as a single system, such that the capturing of the raw digital images and the subsequent processing and handling of the computer vision data is carried out within the single system. Those skilled in the art will appreciate that the resources needed to build these computer vision systems may be quite substantial. Moreover, this approach in which computer vision data is generated and then handled by a single system means that the processing and handling is performed locally. Because the processing and handling of the computer vision data is not portable, the computer vision data may not be readily transferrable to another computing device (and, in some situations, cannot be transferred at all). Accordingly, individuals who are interested in utilizing computer vision data generally reserve time to work with a computer vision system, which may be inconvenient and/or impractical (e.g., due to expense).

Introduced here, therefore, are computer programs that are able to generate computer vision data through local analysis of image data (also referred to as "raw data" or "input data"). The image data may be representative of one or more digital images that are generated by an image sensor. Also introduced here are apparatuses for generating and then handling the image data. These apparatuses are not particularly limited and may be any computing device that is capable of generating and/or handling image data. For convenience, apparatuses that are capable of generating image data may be referred to as "imaging apparatuses," while apparatuses that are capable of handling image data may be referred to as "processing apparatuses." Some computing devices (e.g., computer servers) may only be able to serve as processing apparatuses, while other computing devices (e.g., mobile phones and tablet computers) may be able to serve as imaging apparatuses and/or processing apparatuses.

As further discussed below, one of the advantages of the approach disclosed herein is that a digital image captured from a single point of view can be processing locally (i.e., by the imaging apparatus that generated the digital image), so as to generate computer vision data. Generally, this computer vision data is generated in a portable format that can be readily used by "downstream" computer programs. These computer programs are not particularly limited, and examples include computer programs that are designed to serve a visualization tools, animation tools, and analysis tools (e.g., for diagnostics).

For the purpose of illustration, embodiments may be described in the context of generating computer vision data that is used to derive insights into the spatial positions and movements of a human body. However, features of those embodiments may be similarly applicable to generating computer vision data that is usable in other contexts.

Moreover, embodiments may be described in the context of executable instructions for the purpose of illustration. However, those skilled in the art will recognize that aspects of the technology could be implemented via hardware, firmware, or software. As an example, computer vision data may be obtained by a software-implemented therapy platform (or simply "therapy platform") designed to improve adherence to, and success of, care programs (or simply "programs") assigned to patients for completion. As part of a program, the therapy platform may request that a patient complete a number of exercise therapy sessions (or simply "sessions") in which the patient is instructed to perform physical activities. For example, the patient may be instructed to perform a series of exercises over the course of a session. The therapy platform may determine whether these exercises are completed successfully based on an analysis of the computer vision data. The therapy platform may interface, directly or indirectly, with hardware, firmware, or other software implemented on the same computing device. Additionally or alternatively, the therapy platform may interface, directly or indirectly, with other computing devices as discussed below.

Terminology

References in the present disclosure to "an embodiment" or "some embodiments" mean that the feature, function, structure, or characteristic being described is included in at least one embodiment. Occurrences of such phrases do not necessarily refer to the same embodiment, nor are they necessarily referring to alternative embodiments that are mutually exclusive of one another.

The term "based on" is to be construed in an inclusive sense rather than an exclusive sense. That is, in the sense of "including but not limited to." Thus, unless otherwise noted, the term "based on" is intended to mean "based at least in part on."

The terms "connected," "coupled," and variants thereof are intended to include any connection or coupling between two or more elements, either direct or indirect. The connection or coupling can be physical, logical, or a combination thereof. For example, elements may be electrically or communicatively coupled to one another despite not sharing a physical connection.

The term "module" may refer broadly to software, firmware, hardware, or combinations thereof. Modules are typically functional components that generate one or more outputs based on one or more inputs. A computer program may include or utilize one or more modules. For example, a computer program may utilize multiple modules that are responsible for completing different tasks, or a computer program may utilize a single module that is responsible for completing all tasks.

When used in reference to a list of multiple items, the word "or" is intended to cover all of the following interpretations: any of the items in the list, all of the items in the list, and any combination of items in the list.

Overview of Computer Vision System

FIG. 1 includes a schematic representation of an apparatus 50 configured to generate computer vision data based on raw data that is captured by the apparatus 50. In FIG. 1, the apparatus 50 includes a camera 55, an image analysis engine 60 (or simply "analysis engine"), and a communications interface 65. Other embodiments of the apparatus 50 may include additional components that are not shown here, such as additional interfaces, input devices, or output devices (e.g., indicators) to interact with a user of the apparatus 50. The interactions may include providing output to the user to provide information relating to the operational status of the apparatus 50, as well as receiving input from the user to control the apparatus 50. Examples of input devices include pointer devices, mechanical buttons, keyboards, and microphones to control the apparatus 50 or provide input parameters. Examples of output devices include displays, illuminants, and speakers. In the event that the display is touch sensitive, the display could serve as an input device and output device.

The apparatus 50 can take various forms. In some embodiments, the apparatus 50 is a specially designed computing device that is tailored to capture raw data for which computer vision data is to be generated. In other embodiments, the apparatus 50 is a general purpose computing device. For example, the apparatus 50 could be a mobile phone, tablet computer, laptop computer, desktop computer, or another portable electronic device.

The camera 55 may be responsible for capturing raw data in the form of one or more digital images of an object of interest (e.g., a human body). Generally, these digital images are representative of a video stream that is captured by the camera 55, though these digital images could be independently generated by the camera 55 at different points in time, from different locations, etc. Note that the camera 55 is described for the purpose of illustration, and many different types of image sensors are contemplated. For example, the apparatus 50 may include an image sensor that is designed to cover the infrared, near infrared, visible, or ultraviolet regions.

Generally, the camera 55 is part of the apparatus 50. For example, if the apparatus 50 is a mobile phone or tablet computer, the camera 55 may be the front- or rear-facing camera contained therein. However, the camera 55 may be communicatively connected to the apparatus 50 in some embodiments. For example, the camera 55 may be included in a portable video camera (e.g., a webcam), camcorder, or another portable camera that can be connected, either directly or indirectly, to the apparatus 50. Thus, the camera 55 may be included in the computing device that is responsible for processing digital images that are generated, or the camera 55 may be communicatively connected to the computing device that is responsible for processing digital images that are generated.

Furthermore, it is to be appreciated by one skilled in the art with the benefit of the present disclosure that the raw data is not particularly limited. In the present example, the raw data may be representative of one or more digital images of an object of interest (e.g., a human body). The digital images could be representative of the frames of a video that is captured by the camera 55. Advantageously, the manner in which the object is represented (and the exact format of the raw data) are not particularly limited. For example, each digital image may be a raster graphic file or a compressed image file, for example, formatted in accordance with the MPEG-4 format or JPEG format. In other embodiments, the digital images are formatted in accordance with the RGB format (i.e., where each pixel is assigned a red value, green value, and blue value). Moreover, it is to be appreciated that the raw data is not limited to digital images that are generated using visible light. As mentioned above, the apparatus 50 could instead include an image sensor that is designed to cover the infrared, near infrared, or ultraviolet regions. As such, the raw data may include infrared digital images or ultraviolet digital images instead of, or in addition to, visible digital images. In embodiments, where the raw data includes infrared information and/or ultraviolet information in addition to visible information, the camera 55 may be one of multiple image sensors that observe the object of interest. Image data generated by these multiple image sensors could be stored separately (e.g., as separate digital images), or image data generated by these multiple image sensors could be stored together (e.g., as RGB-D digital images that include a fourth dimension specifying depth on a per-pixel basis).

The object that is captured in the digital images (and thus, represented by the raw data) is also not particularly limited. For the purpose of illustration, embodiments of the present disclosure are described in the context of imaging a person. However, the features of these embodiments may be similarly applicable to other types of objects that may be in motion, such as an animal or machine (e.g., a vehicle or robotic device). Accordingly, the camera 55 may be used to image any object in motion for subsequent processing by the analysis engine 60 provided that the analysis engine 60 has been trained to handle that object.

The analysis engine 60 may be responsible for analyzing the raw data captured by the camera 55. Moreover, the analysis engine 60 may subsequently use the analysis to generate computer vision data. The manner by which the analysis engine 60 analyzes the raw data is not particularly limited. In the present example, the analysis engine 60 is locally executed by a processor of the apparatus 50. Assume, for example, that the apparatus 50 is a mobile phone or tablet computer. Modern computing devices such as these generally have the computational resources needed to carry out an analysis using a model in an efficient manner. The model could be based on a neural network, for example. If the model is representative of a neural network, the neural network that is used by the analysis engine 60 may be trained prior to installation on the apparatus 50 or trained after installation on the apparatus 50 using training data that is available to the apparatus 50 (e.g., via a network such as the Internet). Alternatively, the analysis engine 60 could be remotely executed by a processor that is external to the apparatus 50 as further discussed below.

One skilled in the art will recognize that the type and architecture of the model used by the analysis engine 60 is not particularly limited. As mentioned above, the model may be representative of a neural network that can be used as part of a computer vision-based human pose and segmentation system. As a specific example, the analysis engine 60 may use, or be representative of, the artificial intelligence (AI) engine described in WIPO Publication No. 2020/000096, titled "Human Pose Analysis System and Method," WIPO Publication No. 2020/250046, titled "Method and System for Monocular Depth Estimation of Persons," or WIPO Publication No. 2021/186225, titled "Method and System for Matching 2D Human Poses from Multiple Views," each of which is incorporated by reference herein in its entirety. In other embodiments, the analysis engine 60 may include or utilize a real-time detection library (e.g., OpenPose, Alpha-Pose, or PoseNet), a convolutional neural network (CNN) (e.g., Mask R-CNN), or a depth sensor based on a stereo camera or light detection and ranging (LiDAR) sensor system (e.g., Microsoft Kinect or Intel RealSense).

Accordingly, the analysis engine 60 may generate computer vision data by applying a model to the raw data that is provided as input. Generally, the analysis engine 60 generates the computer vision data as a serialized stream of data. For example, the analysis engine 60 may output "chunks" of computer vision data in real time as digital images generated by the camera 55 are sequentially fed into the model. As mentioned above, these digital images may be representative of the frames of a video feed captured by the camera 55. The computer vision data can take various forms. For example, the computer vision data may include data that is representative of 3D skeletons, 2D skeletons, 3D meshes, and segmentation data. It is to be appreciated with the benefit of the present disclosure that the computer vision data is normally generated in a portable format that allows the computer vision data to be readily transferred to, and handled by, downstream computing devices and computer programs. The portable format can take various forms. For example, the computer vision data could be generated, structured, or compiled in a portable format in accordance with a known data protocol. As another example, the computer vision data could be generated, structured, or compiled in a portable format in accordance with a proprietary data protocol (also referred to as the "wrnch eXchange data protocol" or "wrXchng data protocol") that is developed by the same entity that develops the analysis engine 60. While its content may vary, the portable format generally provides data structures for computer vision data and associated metadata (e.g., timestamps, a source identifier associated with the apparatus that generated the corresponding raw data, information regarding the computer vision data or corresponding raw data such as size, length, etc.). In some embodiments the corresponding raw data is also included in the portable format, while in other embodiments the corresponding raw data is transferred away from the apparatus 50 separate from the portable format.

While not shown in FIG. 1, the apparatus 50 normally includes a memory in which the raw data captured by the camera 55 is stored, at least temporarily, prior to analysis by the analysis engine 60. In particular, the memory may store raw data that includes a series of digital images from which the computer vision data is to be generated. In the present example, the memory may include a video comprising multiple frames, each of which is representative of a digital image, that are captured over a period of time. The quality of the frames may be based on characteristics of the apparatus 50 (e.g., memory space, processing capabilities) or camera 55 (e.g., resolution). Similarly, the frame rate at which the digital images are generated by the camera 55 may be based on characteristics of the apparatus 50 (e.g., memory space, processing capabilities) or camera 55 (e.g., shutter speed). For example, a high-resolution digital image may not be processed quickly enough by the processor and then written to the memory before the next digital image is to be captured as indicated by the frame rate. When the camera 55 is limited by hardware resources, the resolution of digital images that it captures may be lowered or the frame rate at which the digital images are captured may be slowed.

The memory may be used to store other data in addition to the raw data. For example, the memory may store various reference data that can be used by the analysis engine 60. Examples of reference data include heuristics, templates, training data, and model data. Moreover, the memory may be used to store data that is generated by the analysis engine 60. For example, the computer vision data that is generated by the model upon being applied to the raw data may be stored, at least temporarily, in the memory.

Further, it is to be appreciated that the memory may be a single storage medium that is able to maintain multiple databases (e.g., corresponding to different individuals, different exercise sessions, different exercises, etc.). Alternatively, the memory may be multiple storage media that are distributed across multiple computing devices (e.g., a mobile phone or tablet computer in addition to one or more computer servers that are representative of a network-accessible server system).

The memory may also be used to store instructions for general operation of the apparatus 50. As an example, the memory may include instructions for the operating system that are executable by a processor to provide general functionality to the apparatus 50, such as functionality to support various components and computer programs. Thus, the memory may include control instructions to operate various components of the apparatus 50, such as the camera 55, speakers, display, and any other input devices or output devices. The memory may also include instructions to operate the analysis engine 60.

The memory may be preloaded with data, such as training data or instructions to operate components of the apparatus 50. Additionally or alternatively, data may be transferred to the apparatus 50 via the communications interface 65. For example, instructions may be loaded to the apparatus 50 via the communications interface 65. The communications interface 65 may be representative of wireless communication circuitry that enables wireless communication with the apparatus 50, or the communications interface 65 may be representative of a physical interface (also referred to as a "physical port") at which to connect one end of a cable to be used for data transmission.

The communications interface 65 may be responsible for facilitating communication with a destination to which the computer vision data is to be transmitted for analysis. Computer vision data generated by the analysis engine 60 may be forwarded to the communications interface 65 for transmission to another apparatus. As an example, if the apparatus 50 is a mobile phone or tablet computer, then the computer vision data may be forwarded to the communications interface 65 for transmission to a computer server that is part of a network-accessible server system. In some embodiments, the communications interface 65 is part of a wireless transceiver. The wireless transceiver may be configured to automatically establish a wireless connection with the wireless transceiver of the other apparatus. These wireless transceivers may be able to communicate with one another via a bidirectional communication protocol, such as Near Field Communication (NFC), wireless USB, Bluetooth®, Wi-Fi®, a cellular data protocol (e.g., LTE, 3G, 4G, or 5G), or a proprietary point-to-point protocol.

It is to be appreciated by one skilled in the art that the other apparatus (also referred to as an "external apparatus") may be any computing device to which computer vision data can be transferred. For example, the external apparatus could be a visualization system (also referred to as a "visualizer") to render a 3D animation. As another example, the external apparatus could be a diagnostic system (also referred to as a "diagnose") to monitor movement of a person captured in the digital images. As another example, the external apparatus could be an analysis system (also referred to as an "analyzer") to analyze a serialized stream of computer vision data to determine, compute, or otherwise provide metrics associated with motion captured by the camera 55. Accordingly, the apparatus 50 provides a simple manner to capture an object (e.g., a person) in motion and then generate computer vision data in a portable format that can be analyzed by downstream computing devices or computer programs.

FIG. 2 includes a flowchart of a method 200 for generating computer vision data based on raw data. To assist in the explanation of the method 200, it will be presumed that the method 200 is performed by the apparatus 50 of FIG. 1. Indeed, the method 200 may be one way in which the apparatus 50 can be configured. Furthermore, the following discussion of the method 200 may lead to further understanding of the apparatus 50 and its components. It is emphasized that the method 200 may not necessarily be performed in the exact sequence as shown. Various steps may be performed in parallel rather than in sequence, or the various steps may be performed in a different sequence altogether.

Initially, the apparatus 50 can capture raw data using the camera 55 (step 210). The raw data may include one or more digital images of an object of interest. As an example, the digital images may be representative of the frames of a video that is captured while a person is moving about a physical environment. Once received by the apparatus 50, the raw data can be stored in a memory (step 220).

Thereafter, the apparatus 50 can analyze the raw data (step 230). More specifically, the apparatus 50 may provide the raw data to the analysis engine 60 as input, so as to compute, infer, or otherwise obtain information about the person contained in the digital images. The information that is obtained by the apparatus 50 is not particularly limited. For example, the information may include segmentation maps, joint heatmaps, or surface information to form 3D meshes. In some embodiments, the analysis engine 60 may identify a person in each digital image if there are multiple people in that digital image. Said another way, the analysis engine 60 may be able to identify a person of interest from amongst multiple people and then monitor movement of the person of interest. In some situations, the person of interest in a digital image may overlap with other objects (e.g., other people). The analysis engine 60 may be able to separate the various objects prior to analysis of the person of interest, such that the overlapping does not affect its ability to monitor movement of the person of interest.

The apparatus 50 can then generate computer vision data (step 240) based on the information obtained in step 230. In the present example, the computer vision data produced by the analysis engine 60 (and, more specifically, output by a model applied to the raw data, information, or both) can be populated or encoded into a portable data structure (also referred to as "data file") that can be read by other computing devices and computer programs. For instance, the computer vision data could be populated or encoded into a data structure that is formatted in accordance with the wrXchng format, and then the apparatus 50 could transmit the data structure to a destination (step 250). The destination could be another computing device that is communicatively connected to the apparatus, or the destination could be a computer program that is executing on the apparatus 50.

Figure 3:
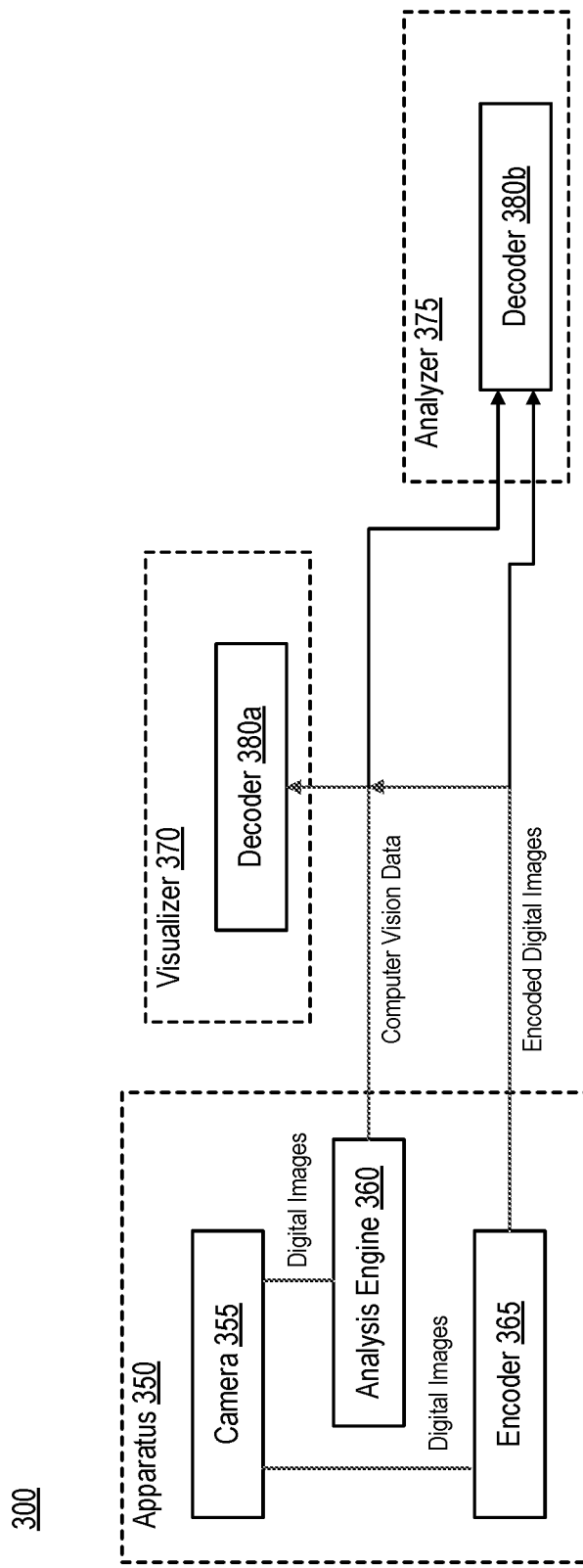
FIG. 3 illustrates an example of a system capable of implementing an apparatus to capture raw data that is associated with an object of interest.

FIG. 3 illustrates an example of a system 300 capable of implementing an apparatus 350 to capture raw data that is associated with an object of interest. It is to be appreciated that the apparatus 350 may be similar to the apparatus 50 of FIG. 1. Accordingly, one skilled in the art will understand with the benefit of the present disclosure that the apparatus 350 of FIG. 3 and the apparatus 50 of FIG. 1 may be substituted for one another.

In the present example, the apparatus 350 includes a camera 355 that is configured to generate digital images which are then fed into an analysis engine 360. As discussed above, the analysis engine 360 may generate computer vision data based on the digital images. For example, the analysis engine 360 may apply a model to each digital image, so as to generate a sequential stream of computer vision data. Generally, the computer vision data is populated or encoded into one or more data structures prior to transmission away from the apparatus 350. As an example, the computer vision data may be encoded into a data structure, and then the data structure may be provided, as input, to an encoder 365 that encodes the data structure that serves as the payload for transmission purposes.

As mentioned above, the computer vision data can be transmitted to one or more downstream computing devices or computer programs. Here, for example, the computer vision data is transmitted to two computing devices, namely, a visualizer 370 and an analyzer 375. In each of the visualizer 370 and analyzer 375, a decoder 380a, 380b may be responsible for decoding the data structure so that the computer vision data contained therein is accessible.

Figure 4:
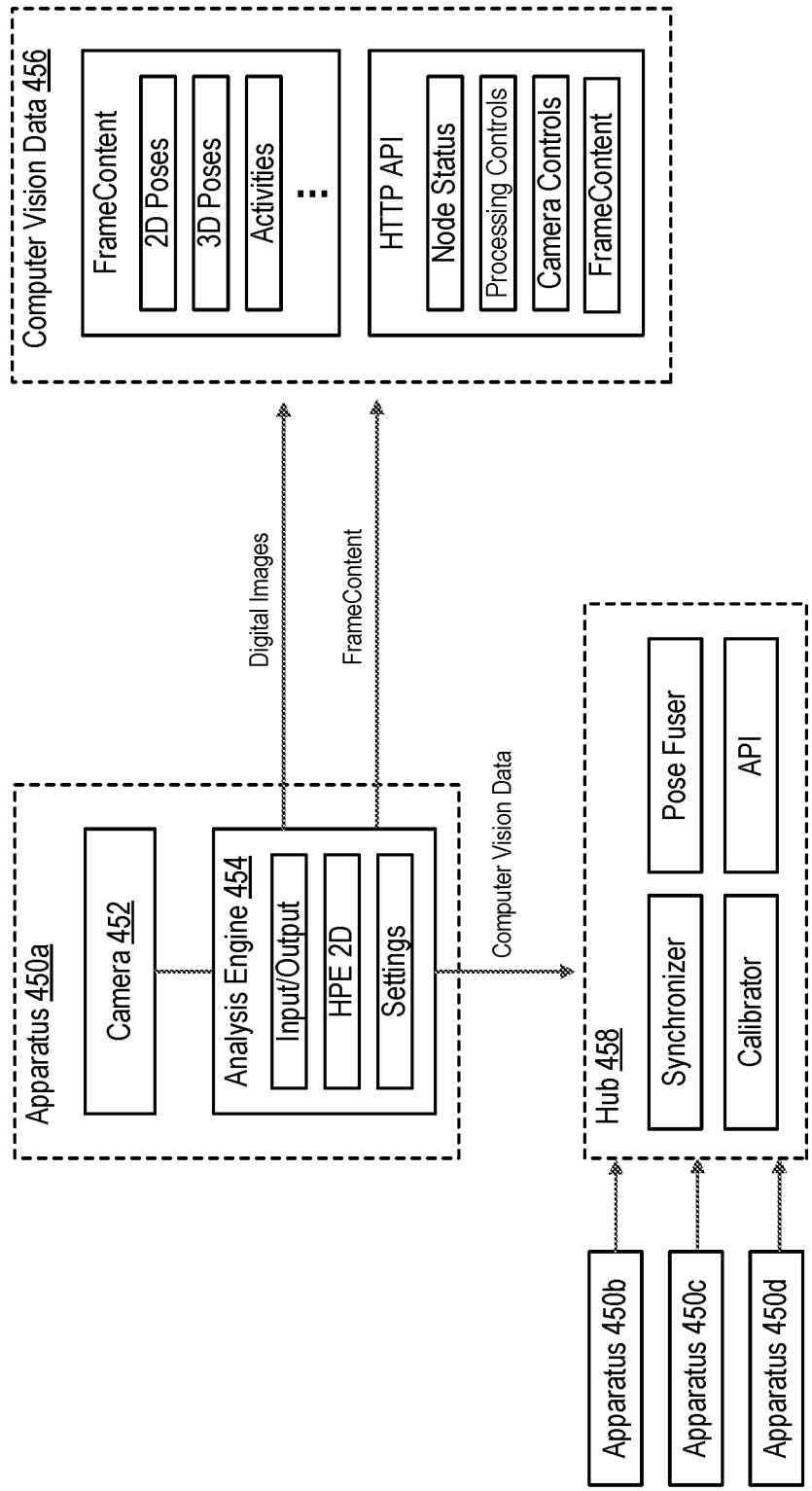
FIG. 4 illustrates an example of a system that includes a plurality of apparatuses that are able to collectively implement the approach described herein.

FIG. 4 illustrates an example of a system 400 that includes a plurality of apparatuses 450a-d that are able to collectively implement the approach described herein. The plurality of apparatuses 450a-d may be collectively referred to as "apparatuses 450" for convenience. Again, the apparatuses 450 may be similar to the apparatus 50 of FIG. 1.

As mentioned above, the computer vision data can be raw, processed, or a combination thereof. Raw computer vision data could include raw or compressed video data, audio data, thermal sensor data, etc. Processed computer vision data could include the locations of anatomical features (e.g., bones, muscles, or joints) in the 2D image plane (e.g., in pixel coordinates), the location of anatomical features in 3D space, 3D joint rotations for humans detected in video data, 2D cutouts of humans depicted in video data (e.g., one image mask per detected human), textual or numeric descriptions of a movement or a series of movements (e.g., that are representative of an activity) performed by humans depicted in video data, 3D voxels representing the shape of humans depicted in video data, and the like.

Note, however, that all of the apparatuses 450 need not necessarily generate raw data. In some embodiments, all of the apparatuses 450 generate raw data, and this raw data can be processed locally (i.e., by the apparatus 450 that generates it) or remotely (e.g., by one of the apparatuses 450 or another computing device, such as a computer server). In other embodiments, a subset of the apparatuses 450 generate raw data. Thus, each apparatus 450 may be able to generate raw data and/or generate computer vision data.

In the present example, apparatus 450a includes a camera 452 to capture digital images which are then fed into an analysis engine 454. The computer vision data 456 produced by the analysis engine 454 as output can then be subsequently transmitted to a downstream destination. For example, the computer vision data 456 may be transmitted to another computing device that acts as a hub apparatus 458 (or simply "hub") for collecting computer vision data from multiple sources. Each source may be representative of a different one of the apparatuses 450 that generates raw data from a different angle (and thus, a different perspective). In order to synchronize the computer vision data acquired from the multiple sources, the hub 458 may examine timestamps appended to the computer vision data by each source. Accordingly, the hub 458 may be used to combine the computer vision data 456 received from multiple apparatuses 450 to generate a "blended" 3D dataset that may be more accurate than if computer vision data is generated from a single point of view. Thus, the implementation shown in FIG. 4 may allow a user to deploy multiple apparatuses 450 to obtain computer vision data 456 of high quality.

FIG. 5 illustrates an example of system 500 in which an apparatus 550 is communicatively connected to another computing device that acts as a visualizer 558. Again, the apparatus 550 may be similar to the apparatus 50 of FIG. 1. In the present example, the apparatus 550 includes a camera 552 to capture digital images which are fed to an analysis engine 554. The analysis engine 554 may produce computer vision data as output, and the computer vision data can subsequently be transmitted (e.g., via an Internet connection 556) to a visualizer 558 along with the digital images (e.g., in the form of a video file 560) or metadata 562. The metadata 562 may identify the apparatus 550 as the source of the digital images or computer vision data. The metadata 562 can be appended to the digital images or computer vision data prior to its transmission to the visualizer 558. The visualizer 558 may cause display of the video file 560 on an interface 564 in addition to, or instead of, analyses of the computer vision data. As an example, the visualizer 558 may display the computer vision data, or analyses of the computer vision data, so as to visually indicate movement of the object of interest (e.g., a person).

FIG. 6 illustrates an example of a system 600 in which an apparatus 650 is communicatively connected to a network-accessible resource 658 (also referred to as a "cloud-based resource" or simply "cloud"). Again, the apparatus 650 may be similar to the apparatus 50 of FIG. 1. In the present example, the apparatus 650 includes a camera 652 to capture digital images which are fed to an analysis engine 654. The analysis engine 654 may produce computer vision data as output, and the computer vision data can subsequently be transmitted (e.g., via an Internet connection 656) to another computing device via the cloud 658 along with digital images (e.g., in the form of a video file 660) or metadata 662. The cloud 658 may simply store the computer vision data in a memory 664 in preparation for retrieval by another computing device that processes the computer vision data. Alternatively, the cloud 658 may process the computer vision data. Accordingly, the computer vision data may be provided to another party as a service based on a computer program that the party downloads to a computing device.

Figure 7:
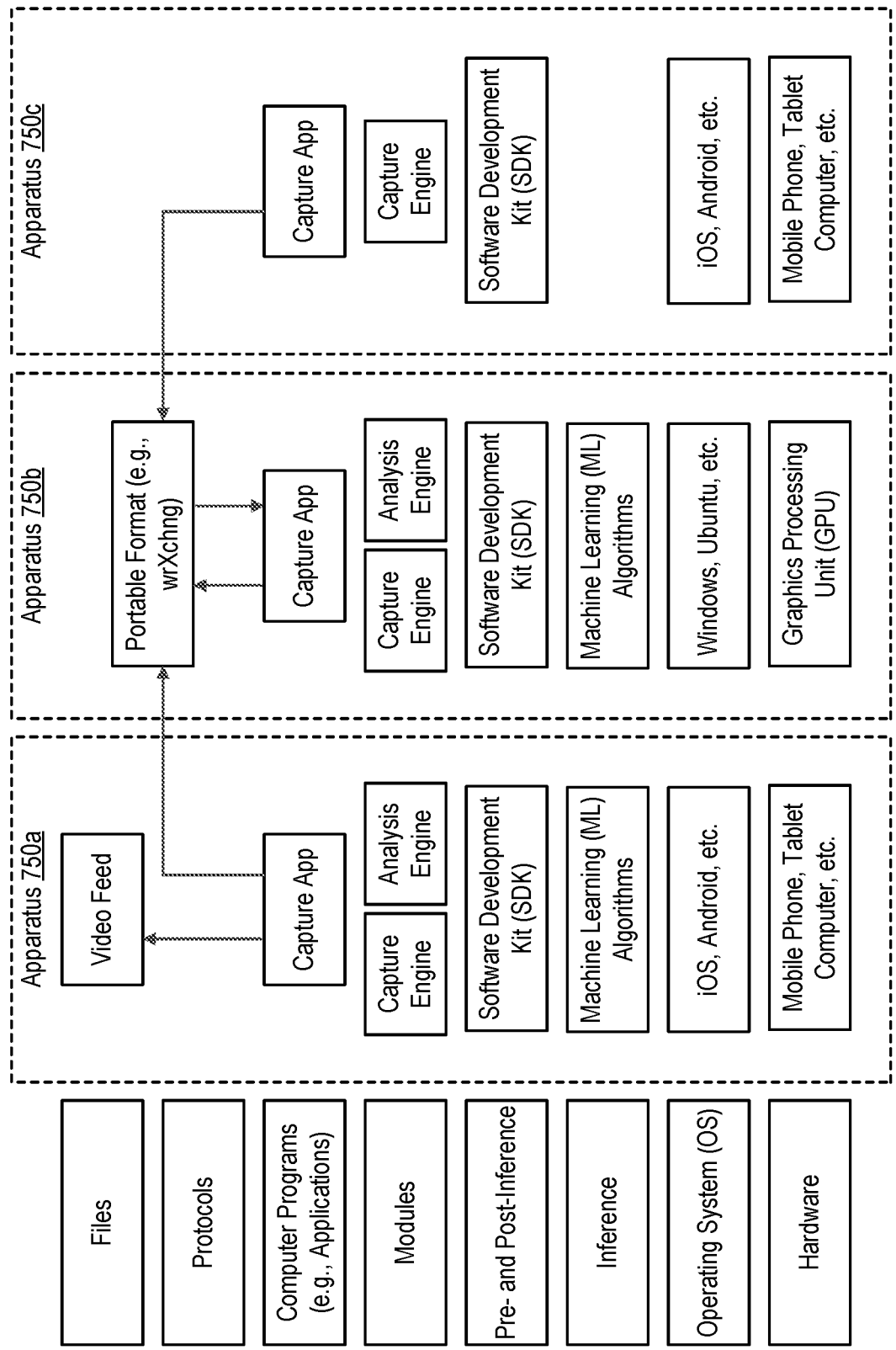
FIG. 7 illustrates three different implementations of an apparatus.

FIG. 7 illustrates three different implementations of an apparatus 750a-c. Again, the apparatuses 750a-c may be similar to the apparatus 50 of FIG. 1. In the present example, apparatus 750a is implemented on a computing device that executes an operating system (e.g., an iOS operating system developed by Apple Inc. or an Android operating system developed by Google LLC), apparatus 750b is implemented on a more sophisticated computing device (e.g., that includes a graphics processing unit (GPU) and executes a Windows operating system developed by Microsoft Corp.), and another apparatus 750c is implemented on a computing device that executes an operating system (e.g., an iOS operating system developed by Apple Inc. or an Android operating system developed by Google LLC). As can be seen in FIG. 7, the computer programs (also referred to as "capture applications" or "capture apps") executing on apparatuses 750a-b include both a capture engine and an analysis engine. As such, these capture applications may be able to receive raw data (e.g., a video feed) as input and then produce computer vision data as output. Conversely, the capture application executing on apparatus 750 only includes a capture engine. As such, raw data that is obtained by the capture engine may be forwarded to another capture application executing on another apparatus (e.g., apparatus 750b in this example) for analysis.

Figure 8:
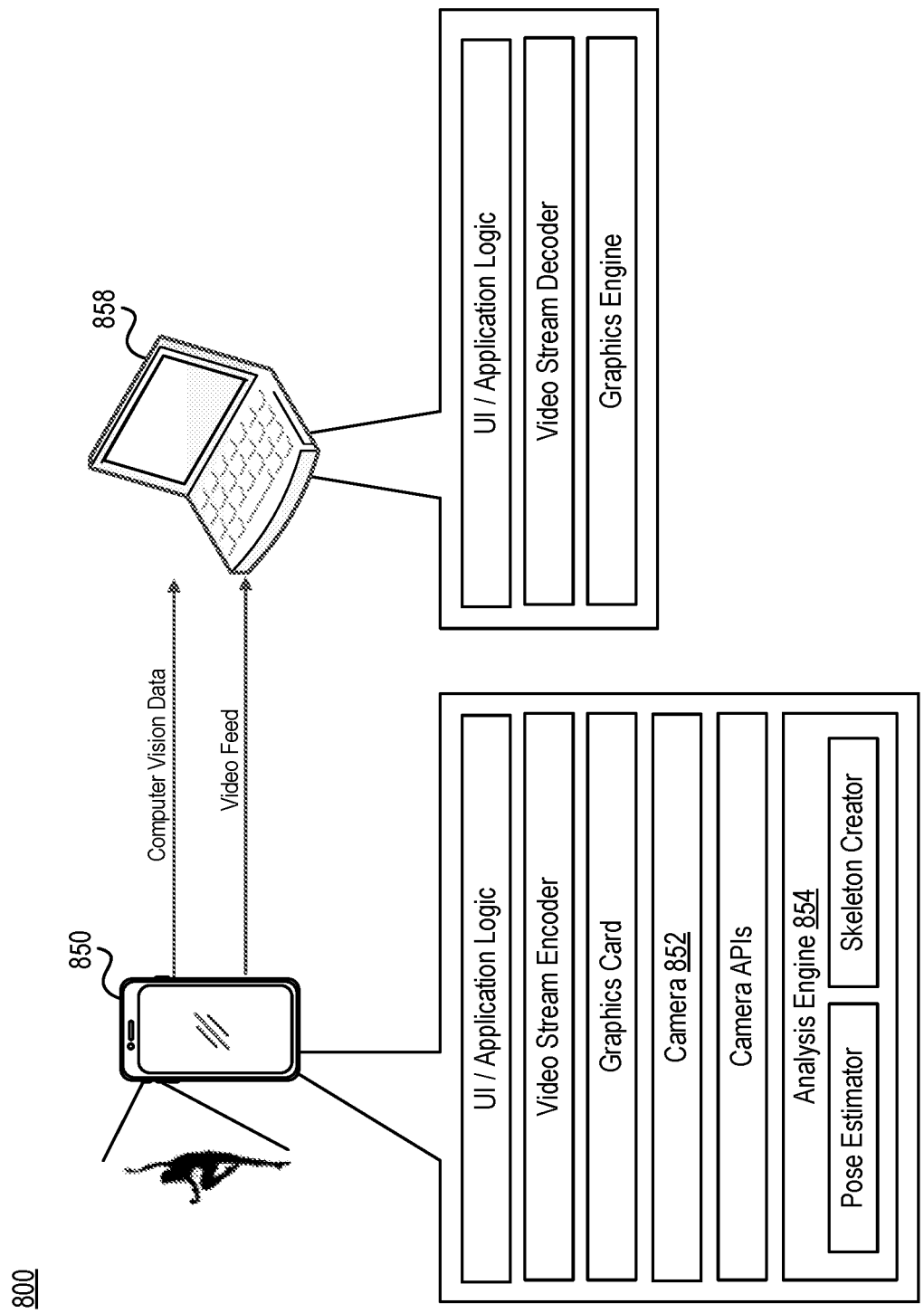
FIG. 8 illustrates an example of a system in which an apparatus is a mobile phone that is communicatively connected to a laptop computer.

FIG. 8 illustrates an example of a system 800 in which an apparatus 850 is a mobile phone that is communicatively connected to a laptop computer 858. Those skilled in the art will recognize that other types of computing devices, such as tablet computers or desktop computers, could be used instead of the laptop computer 858. The apparatus 850 may be similar to the apparatus 50 of FIG. 1.

In embodiments where the apparatus 850 is a mobile phone with a camera 852, digital images generated by the camera 852 (e.g. a video of a person performing an activity, such as exercising, dancing, etc.) can be fed to an analysis engine 854 that is implemented by a mobile application executing on the mobile phone. Computer vision data generated by the analysis engine 854 may be subsequently transmitted (e.g., via Wi-Fi) to another computer program 856 executing on the laptop computer 858 for analysis. The computer vision data may be accompanied by the digital images generated by the camera 852 that is to be displayed by the laptop computer 858. Accordingly, the other computer program 856 executing on the laptop computer 858 may be representative of a visualizer.

Figure 9:
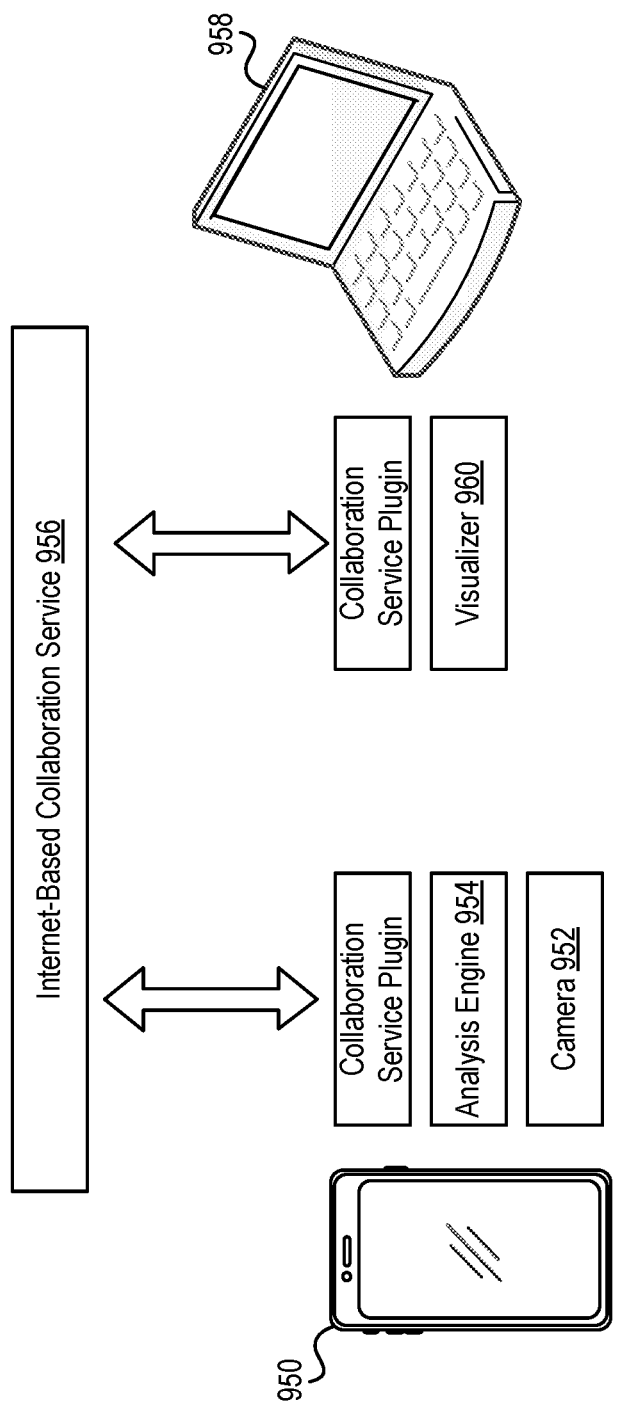
FIG. 9 illustrates an example of a system in which an apparatus is a mobile phone that is communicatively connected to an Internet-based collaboration service that allows information (e.g., raw data or computer vision data) to be readily shared amongst different computing devices.

FIG. 9 illustrates an example of a system 900 in which an apparatus 950 is a mobile phone that is communicatively connected to an Internet-based collaboration service that allows information (e.g., raw data or computer vision data) to be readily shared amongst different computing devices. Again, those skilled in the art will recognize that another type of computing device could be used instead of the mobile phone and laptop computer. For example, the apparatus 950 may be a tablet computer that is configured to upload computer vision data to a computer server for analysis.

In embodiments where the apparatus 950 is a mobile phone with a camera 952, digital images generated by the camera 952 (e.g., a video of a person performing an activity, such as exercising, dancing, etc.) can be provided to an analysis engine 954 as input. As shown in FIG. 9, the analysis engine 954 may be executed via an Internet-based collaboration service 956 (e.g., LiveLink) that allows the computer vision data produced as output to be provided to a downstream computing device or computer program. Here, for example, the computer vision data is provided to a visualizer 960 executing on a laptop computer 958.

Overview of Therapy Platform

Figure 10:
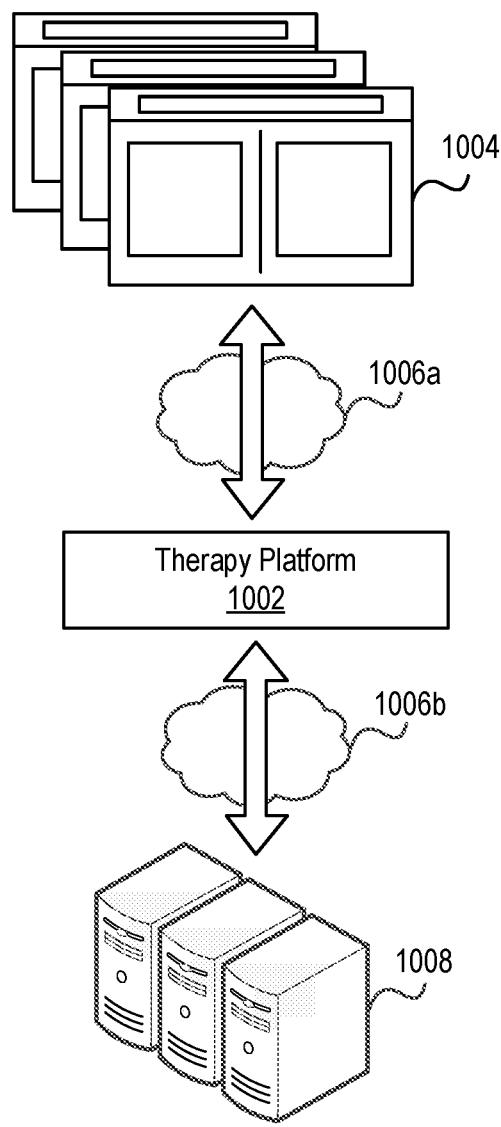
FIG. 10 illustrates an example of a network environment that includes a therapy platform.
Figure 11:
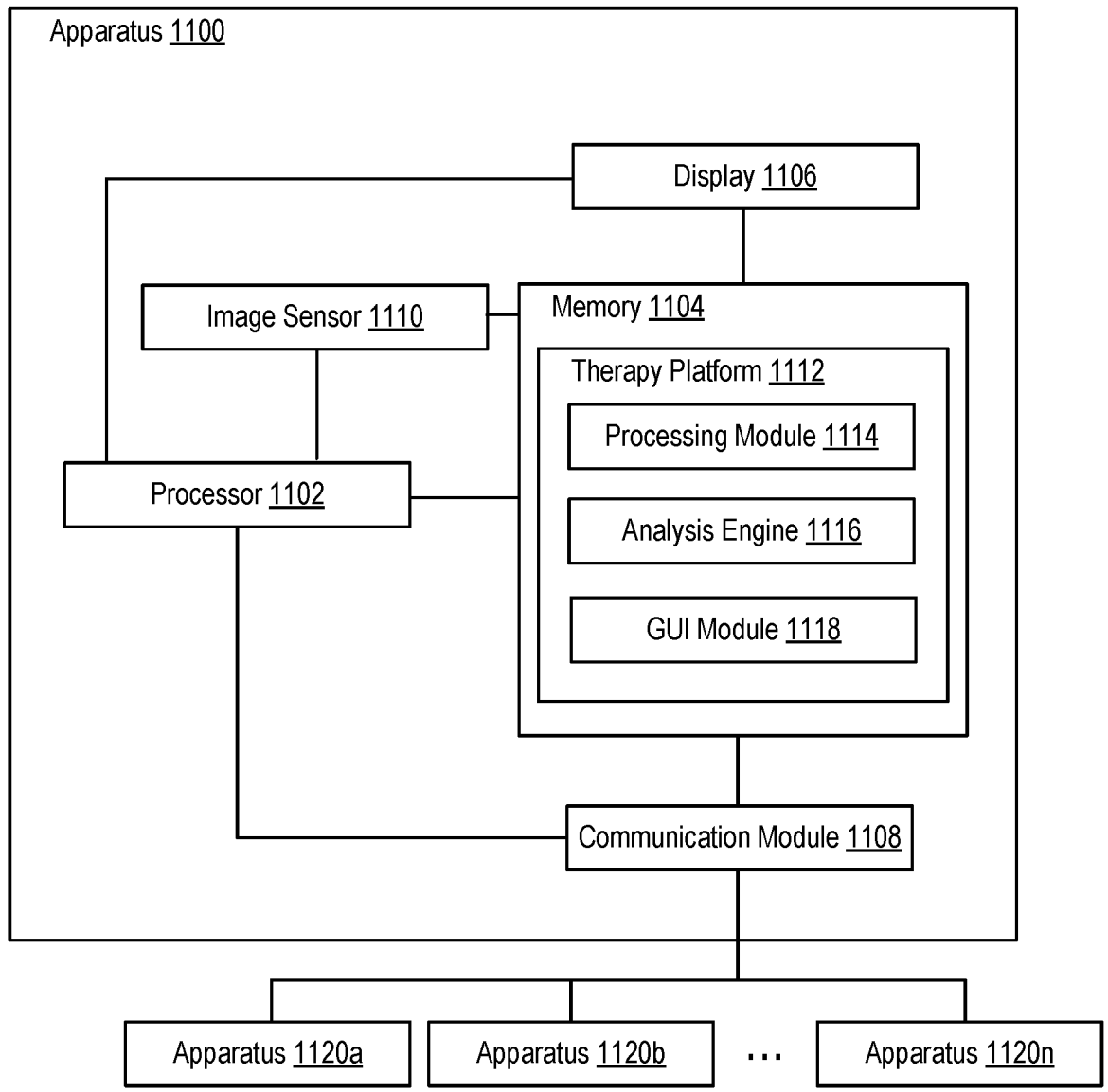
FIG. 11 illustrates an example of an apparatus able to implement a program in which a patient is requested to perform physical activities, such as exercises, during exercise therapy sessions by a therapy platform.
Figure 12:
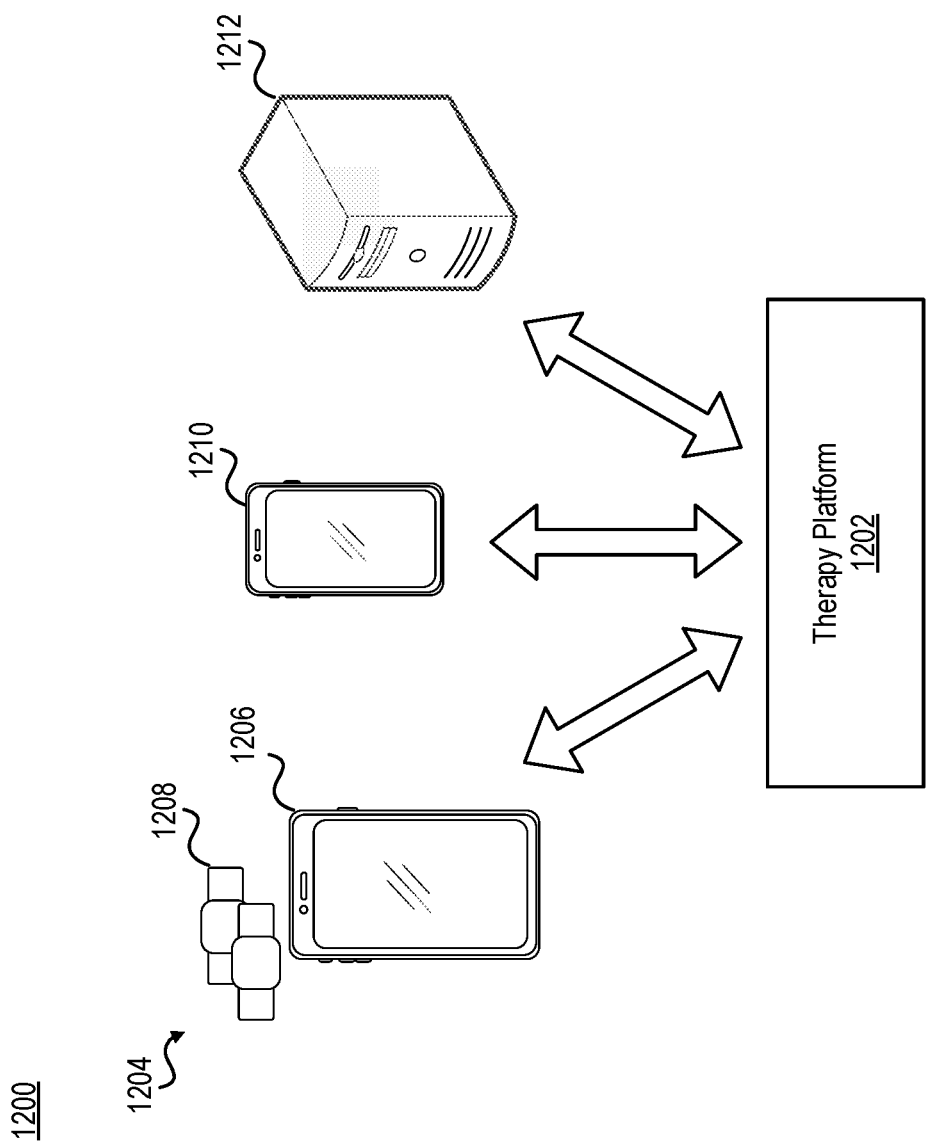
FIG. 12 depicts an example of a communication environment that includes a therapy platform configured to obtain data from one or more sources.

As mentioned above, the computer vision data that is produced by an analysis engine (e.g., analysis engine 60 of FIG. 1) can be used by various downstream computing devices and computer programs. One example of such a computer program is a therapy platform designed to improve adherence to, and success of, care programs (or simply "programs") assigned to patients for completion. In FIGS. 10-12, features are described in the context of a therapy platform that is responsible for guiding a patient through sessions that are performed as part of a program. However, those skilled in the art will recognize that the computer vision data could be used in various other ways as discussed above.

FIG. 10 illustrates an example of a network environment 1000 that includes a therapy platform 1002. Individuals can interact with the therapy platform 1002 via interfaces 1004. For example, patients may be able to access interfaces that are designed to guide them through sessions, present educational content, indicate progression in a program, present feedback from coaches, etc. As another example, healthcare professionals may be able to access interfaces through which information regarding completed sessions (and thus program completion) and clinical data can be reviewed, feedback can be provided, etc. Thus, interfaces 1004 generated by the therapy platform 1002 may serve as informative spaces for patients or healthcare professionals or collaborative spaces through which patients and healthcare professionals can communicate with one another.

As shown in FIG. 10, the therapy platform 1002 may reside in a network environment 1000. Thus, the apparatus that the therapy platform 1002 is executing on may be connected to one or more networks 1006a-b. The apparatus could be apparatus 50 of FIG. 1, or the apparatus could be communicatively connected to apparatus 50 of FIG. 1. The networks 1006a-b can include personal area networks (PANs), local area networks (LANs), wide area networks (WANs), metropolitan area networks (MANs), cellular networks, the Internet, etc. Additionally or alternatively, the apparatus can be communicatively coupled to other apparatuses over a short-range wireless connectivity technology, such as Bluetooth, Near Field Communication (NFC), Wi-Fi Direct (also referred to as "Wi-Fi P2P"), and the like. As an example, the therapy platform 1002 is embodied as a mobile application that is executable by a tablet computer in some embodiments. In such embodiments, the tablet computer may be communicatively connected to a mobile phone that generates raw data via a short-range wireless connectivity technology and a computer server that stores or handles computer vision data via the Internet.

In some embodiments, at least some components of the therapy platform 1002 are hosted locally. That is, part of the therapy platform 1002 may reside on the apparatus used to access one of the interfaces 1004. For example, the therapy platform 1002 may be embodied as a mobile application executing on a mobile phone or tablet computer. Note, however, that the mobile application may be communicatively connected to a network-accessible server system 1008 on which other components of the therapy platform 1002 are hosted.

In other embodiments, the therapy platform 1002 is executed entirely by a cloud computing service operated by, for example, Amazon Web Services® (AWS), Google Cloud Platform™, or Microsoft Azure®. In such embodiments, the therapy platform 1002 may reside on a network-accessible server system 1008 comprised of one or more computer servers. These computer servers can include information regarding different programs, sessions, or physical activities; models for generating computer vision data based on an analysis of raw data (e.g., digital images); models for establishing movement of an object (e.g., a person) based on an analysis of computer vision data; algorithms for processing raw data; patient data such as name, age, weight, ailment, enrolled program, duration of enrollment, number of sessions completed, and correspondence with coaches; and other assets. Those skilled in the art will recognize that this information could also be distributed amongst multiple apparatuses. For example, some patient data may be stored on, and processed by, her own mobile phone for security and privacy purposes. This information may be processed (e.g., obfuscated) before being transmitted to the network-accessible server system 1008. As another example, the algorithms and models needed to process raw data or computer vision data may be stored on the apparatus that generates such data to ensure that such data can be processed in real time (e.g., as physical activities are being performed as part of a session).

FIG. 11 illustrates an example of an apparatus 1100 able to implement a program in which a patient is requested to perform physical activities, such as exercises, during sessions by a therapy platform 1112. In some embodiments, the therapy platform 1112 is embodied as a computer program that is executed by the apparatus 1100. In other embodiments, the therapy platform 1112 is embodied as a computer program that is executed by another apparatus (e.g., a computer server) to which the apparatus 1100 is communicatively connected. In such embodiments, the apparatus 1100 may transmit relevant information, such as raw data, computer vision data, or inputs provided by a patient, to the other apparatus for processing. Those skilled in the art will recognize that aspects of the computer program could also be distributed amongst multiple apparatuses.

The apparatus 1100 can include a processor 1102, memory 1104, display 1106, communication module 1108, image sensor 1110, or any combination thereof. Each of these components is discussed in greater detail below. Those skilled in the art will recognize that different combinations of these components may be present depending on the nature of the apparatus 1100.

The processor 1102 can have generic characteristics similar to general-purpose processors, or the processor 1102 may be an application-specific integrated circuit (ASIC) that provides control functions to the apparatus 1100. As shown in FIG. 11, the processor 1102 can be coupled to all components of the apparatus 1100, either directly or indirectly, for communication purposes.

The memory 1104 may be comprised of any suitable type of storage medium, such as static random-access memory (SRAM), dynamic random-access memory (DRAM), electrically erasable programmable read-only memory (EEPROM), flash memory, or registers. In addition to storing instructions that can be executed by the processor 1102, the memory 1104 can also store data generated by the processor 302 (e.g., when executing the modules of the therapy platform 1112), obtained by the communication module 1108, or created by the image sensor 1110. Note that the memory 104 is merely an abstract representation of a storage environment. The memory 104 could be comprised of actual memory chips or modules.

The display 1106 can be any mechanism that is operable to visually convey information to a user. For example, the display 1106 may be a panel that includes light-emitting diodes (LEDs), organic LEDs, liquid crystal elements, or electrophoretic elements. In some embodiments, the display 1106 is touch sensitive. Thus, a user may be able to provide input to the therapy platform 1112 by interacting with the display 1106.

The communication module 1108 may be responsible for managing communications between the components of the apparatus 1100, or the communication module 1108 may be responsible for managing communications with other apparatuses (e.g., server system 1108 of FIG. 11). The communication module 1108 may be wireless communication circuitry that is designed to establish communication channels with other apparatuses. Examples of wireless communication circuitry include integrated circuits (also referred to as "chips") configured for Bluetooth, Wi-Fi, NFC, and the like. Referring to FIG. 1, the communication module 1108 may support or initiate the communications interface 65, or the communication module 1108 may be representative of the communications interface 65.

The image sensor 1110 may be any electronic sensor that is able to detect and convey information in order to generate image data. Examples of image sensors include charge-coupled device (CCD) sensors and complementary metal-oxide semiconductor (CMOS) sensors. The image sensor 1110 may be implemented in a camera that is implemented in the apparatus 1100. In some embodiments, the image sensor 1110 is one of multiple image sensors implemented in the apparatus 1100. For example, the image sensor 1110 could be included in a front- or rear-facing camera on a mobile phone or tablet computer.

For convenience, the therapy platform 1112 is referred to as a computer program that resides within the memory 1104. However, the therapy platform 1112 could be comprised of software, firmware, or hardware that is implemented in, or accessible to, the apparatus 1100. In accordance with embodiments described herein, the therapy platform 1112 may include a processing module 1114, analysis engine 1116, and graphical user interface (GUI) module 1118. Each of these modules can be an integral part of the therapy platform 1112. Alternatively, these modules can be logically separate from the therapy platform 1112 but operate "alongside" it. Together, these modules enable the therapy platform 1112 to establish the movements of an object of interest (e.g., a person) through analysis of computer vision data associated with raw data generated by the image sensor 1110.

The processing module 1114 can process data that is obtained by the therapy platform 1112 over the course of a session into a format that is suitable for the other modules. For example, the processing module 1114 may apply operations to digital images generated by the image sensor 1110 in preparation for analysis by the other modules of the therapy platform 1112. Thus, the processing module 1114 may despeckle, denoise, or otherwise filter digital images generated by the image sensor 1110. Additionally or alternatively, the processing module 1116 may adjust the properties like contrast, saturation, and gain in order to improve the outputs produced by the other modules of the therapy platform 1112.

As mentioned above, the therapy platform 1112 could receive raw data or computer vision data from one or more other apparatuses 1120*a*-*n* in some embodiments. For example, the apparatus 1100 may receive raw data or computer vision data from another apparatus 1120*a* that monitors the person from another perspective. In embodiments where the therapy platform 1112 obtains raw data or computer vision data from at least one other source, the processing module 1114 may also be responsible for temporally aligning these data with each other.

The analysis engine 1116 may be responsible for generating computer vision data based on the raw data that is generated by image sensor 1110. The analysis engine 1116 of FIG. 11 may be similar to the analysis engine 60 of FIG. 1. In addition to generating the computer vision data, the analysis engine 1116 may be able to compute, infer, or otherwise determine observations related to health of the person under observation from the computer vision data.

Assume, for example, that the analysis engine 1116 obtains 2D skeletons of the person that are created based on raw data generated by multiple apparatuses. These 2D skeletons can be "fused" to create a 3D skeleton for the person. This 3D skeleton may be used to better understand the health state of the person. For example, this 3D skeleton may be used to perform fall detection, gait analysis, activity analysis (e.g., by establishing level of effort), fine motor movement analysis, range of motion analysis, and the like.

As another example, the computer vision data may be representative of musculoskeletal data (e.g., indicating the size and position of muscles, bones, etc.) from a number of apparatuses that are oriented toward completely overlapping, partially overlapping, or non-overlapping areas of a physical environment. The musculoskeletal data could be processed by the analysis engine 1116 using algorithms to produce a more precise series of musculoskeletal data over a period of time (e.g., several seconds or minutes) for some or all of the individuals situated in the physical environment. This musculoskeletal data could be used to better understand the health state of these individuals. For example, this musculoskeletal data may be used to perform fall detection, gait analysis, activity analysis (e.g., by establishing an estimated level of effort), fine motor movement analysis, range of motion analysis, muscle fatigue estimation (e.g., by establishing an estimated level of fatigue being experienced by a muscle), muscle distribution analysis (e.g., to detect atrophy or abnormalities), body mass index (BMI) analysis, and the like.

As another example, the computer vision data may be representative of musculoskeletal data in combination with thermal imaging data and/or non-invasive imaging data (e.g., terahertz imagery) from a number of apparatuses that are oriented toward completely overlapping, partially overlapping, or non-overlapping areas of a physical environment. These data could be processed by the analysis engine 1116 using algorithms to produce more precise musculoskeletal data, vascular flow data, and body shape data over a period of time (e.g., several seconds or minutes) for some or all of the individuals situated in the physical environment. These data could be used to better understand the health state of these individuals. For example, these data may be used to perform fall detection, gait analysis, activity analysis (e.g., by establishing an estimated level of effort), fine motor movement analysis, range of motion analysis, muscle fatigue estimation (e.g., by establishing an estimated level of fatigue being experienced by a muscle), muscle distribution analysis (e.g., to detect atrophy or abnormalities), BMI analysis, blood flow analysis (e.g., by establishing an estimated speed or volume of blood flow, so as to indicate whether blood flow is abnormal), body heat analysis (e.g., by establishing temperature along the surface of a body in one or more anatomical regions, so as to identify warm and cool anatomic regions), and the like.

The GUI module 1118 may be responsible for generating interfaces that can be presented on the display 1106. Various types of information can be presented on these interfaces. For example, information that is calculated, derived, or otherwise obtained by the analysis engine 1116 (e.g., based on analysis of computer vision data) may be presented on an interface for display to a patient or healthcare professional. As another example, visual feedback may be presented on an interface so as to indicate to a patient how to move about a physical environment while raw data is generated by the image sensor 1110.

FIG. 12 depicts an example of a communication environment 1200 that includes a therapy platform 1202 configured to obtain data from one or more sources. Here, the therapy platform 1202 may obtain data from a therapy system 1204 comprised of a tablet computer 1206 and one or more sensor units 1208, mobile phone 1210, or network-accessible server system 1212 (collectively referred to as the "networked devices"). During a session, the therapy platform 1202 may obtain various data, including image data generated by the tablet computer, motion data generated by the sensor units 1208, image data generated by the mobile phone 1210, and other information (e.g., therapy regimen information, models of exercise-induced movements, feedback from healthcare professionals, and processing operations) from the network-accessible server system 1212. Those skilled in the art will recognize that the nature of the data obtained by the therapy platform 1202—as well as the number of sources from which the data is obtained—will depend on its deployment.

The networked devices can be connected to the therapy platform 1202 via one or more networks. These networks can include PANs, LANs, WANs, MANs, cellular networks, the Internet, etc. Additionally or alternatively, the networked devices may communicate with one another over a short-range wireless connectivity technology. For example, if the therapy platform 1202 resides on the tablet computer 1206, motion data may be obtained from the sensor units 1208 over a first Bluetooth communication channel, image data may be obtained from the mobile phone 1210 over a second Bluetooth communication channel, and information may be obtained from the network-accessible server system 1212 over the Internet via a Wi-Fi communication channel.

Embodiments of the communication environment 1200 may include a subset of the networked devices. For example, the communication environment 1200 may not include any sensor units 1208. In such embodiments, the therapy platform 1202 may monitor movement of a person in real time based on analysis of image data generated by the tablet computer 1206 and/or image data generated by the mobile phone 1210.

Determining Health Status Through Analysis of Computer Vision Data

FIG. 13 includes a flowchart of a method 1300 for determining the health status of an individual through analysis of computer vision data. Initially, a therapy platform can acquire a series of digital images generated by an image sensor in rapid succession of a physical environment in which a patient is situated (step 1310). The series of digital images may be representative of the frames of a video file that is generated by the image sensor. Generally, the therapy platform is implemented on the same apparatus as the image sensor. That need not necessarily be the case, however. For example, if the therapy platform is implemented, at least partially, on a computer server that is accessible via a network (e.g., the Internet), then the series of digital images may need to traverse the network to reach the therapy platform.

The therapy platform can then apply a model to the series of digital images to produce a series of outputs (step 1320). Each output in the series of outputs may be representative of information regarding a spatial position of the individual as determined through analysis of a corresponding digital image of the series of digital images. For example, the model may be trained to estimate, for each digital image, a pose of the patient so as to establish serialized poses of the individual over the interval of time over which the series of digital images are generated. The series of outputs may be collectively representative of computer vision data that is output by the model.

The computer vision data can take various forms. In some embodiments, the computer vision data indicates, for each digital image, 2D locations of one or more joints of the patient. In other embodiments, the computer vision data indicates, for each digital image, 3D locations of one or more joints of the patient. Additionally or alternatively, the computer vision data may indicate, for each digital image, 3D rotation of one or more joints of the patient. A skeleton that is representative of the patient may be reconstructed in two or three dimensions based on the locations and/or rotations. Depending on the intended application, other types of computer vision data could be generated instead of, or in addition to, those mentioned above. For example, the computer vision data may indicate, for each digital image, a location, size, or shape of one or more muscles of the patient. This information may be helpful in establishing whether muscular distribution is unusual, as well as determining the level of effort that is being exerted by the patient. As another example, the computer vision data may include a thermal map that is representative of a surface of a body of the patient. This information may be helpful in determining whether blood flow and temperature are unusual. As another example, the computer vision data may include a volumetric representation of the patient that is comprised of voxels, each of which represents a location whose spatial position is determined by the model. This information may be helpful in establishing whether muscular distribution is unusual, as well as measuring BMI.

Thereafter, the therapy platform can assess, based on the computer vision data, health of the individual in real time (step 1330). The nature of the assessment may depend on the type of health insights that are designed. Assume, for example, that the therapy platform is tasked with determining musculoskeletal performance of the patient. In such a scenario, the therapy platform may receive input indicative of a request to initiate a session, cause presentation of an instruction to the individual to perform an exercise, and monitor performance of the exercise through analysis of the computer vision data. Using the computer vision data, the therapy platform may be able to monitor progress of the patient through the session and then take appropriate action. For example, in response to a determination that the individual completed the exercise, the therapy platform may instruct the individual to perform another exercise. As another example, in response to a determination that the individual did not complete the exercise, the therapy platform may provide visual or audible feedback in support of the individual.

Then, the therapy platform can perform an action based on the health of the patient (step 1340). For example, the therapy platform may transmit the computer vision data, or analyses of the computer vision data, onward to a destination. For example, this data could be forwarded onward for further analysis, or this data could be forwarded onward for presentation (e.g., to the patient or a healthcare professional). As another example, the therapy platform may determine whether the patient is representative of an ailment based on the assessed health state. For example, the therapy platform could stratify the patient amongst a series of classifications (e.g., moderate, mild, severe) based on the assessed health state and then determine an appropriate treatment regimen based on classification.

Generally, the therapy platform stores information regarding the health of the individual in a data structure that is associated with the individual. This data structure may be representative of a digital profile in which information regarding the health of the individual is stored and then maintained over time.

While the method 1300 is described in the context of a therapy platform executed by a single apparatus that generates digital images and produces computer vision data based on the digital images, those skilled in the art will recognize that aspects of the method 1300 could be performed by more than one apparatus. In some embodiments, the method 1300 is performed by a system comprised of (i) a plurality of imaging apparatuses that are deployed in an environment in which an individual is situated and (ii) a processing apparatus that assesses the health of the individual based on an analysis of data (e.g., raw data or computer vision data) received from the plurality of imaging apparatuses. In such embodiments, the therapy platform may acquire multiple series of digital images, each of which is generated by a corresponding imaging apparatus. As mentioned above, a single apparatus may be able to image the individual and analyze corresponding data. Accordingly, at least one of the plurality of imaging apparatuses and the processing apparatus could be representative of a single computing device.

Processing System

Figure 14:
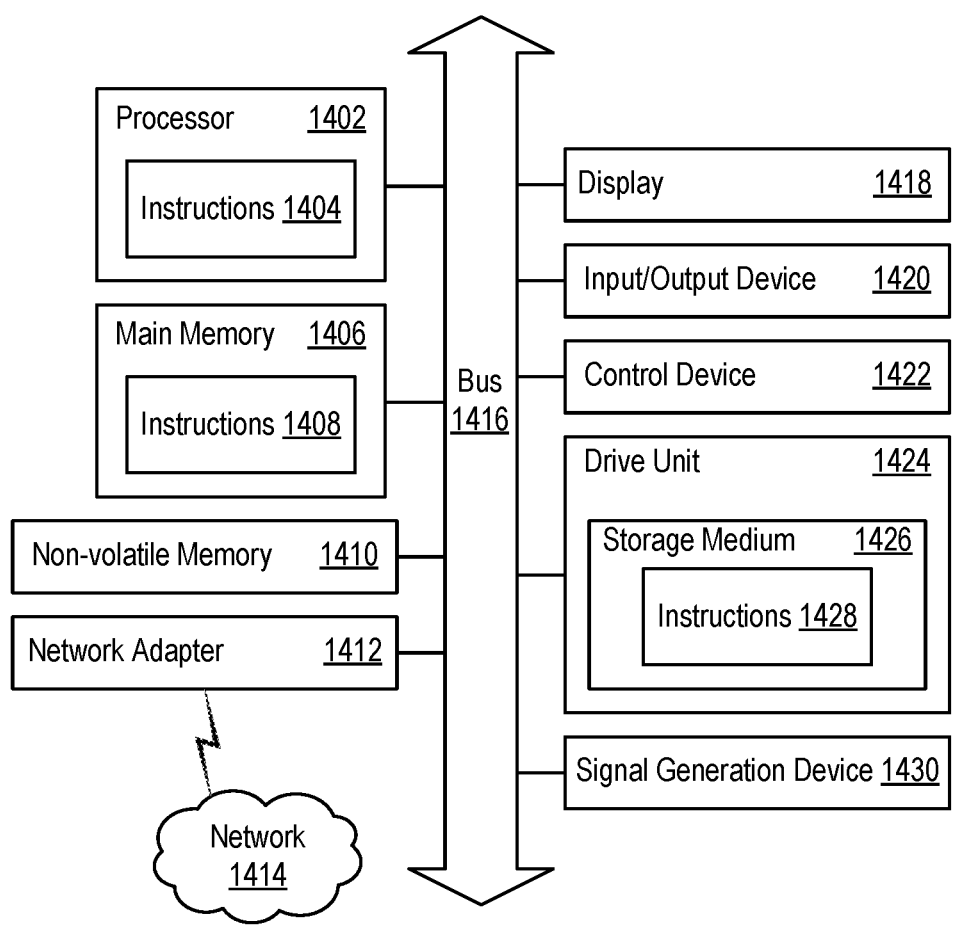
FIG. 14 is a block diagram illustrating an example of a processing system in which at least some operations described herein can be implemented.

FIG. 14 is a block diagram illustrating an example of a processing system 1400 in which at least some operations described herein can be implemented. For example, components of the processing system 1400 may be hosted on an apparatus (e.g., apparatus 50 of FIG. 1) that generates raw data, creates computer vision data, or analyzes computer vision data.

The processing system 1400 may include a processor 1402, main memory 1406, non-volatile memory 1410, network adapter 1412, display 1418, input/output device 1420, control device 1422, drive unit 1424 including a storage medium 1426, and signal generation device 1430 that are communicatively connected to a bus 1416. The bus 1416 is illustrated as an abstraction that represents one or more physical buses or point-to-point connections that are connected by appropriate bridges, adapters, or controllers. The bus 1416, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), inter-integrated circuit ($I^2C$) bus, or an Institute of Electrical and Electronics Engineers (IEEE) standard 1394 bus (also referred to as "Firewire").

While the main memory 1406, non-volatile memory 1410, and storage medium 1426 are shown to be a single medium, the terms "machine-readable medium" and "storage medium" should be taken to include a single medium or multiple media (e.g., a centralized/distributed database and/or associated caches and servers) that store one or more sets of instructions 1428. The terms "machine-readable medium" and "storage medium" shall also be taken to include any medium that is capable of storing, encoding, or carrying a set of instructions for execution by the processing system 1400.

In general, the routines executed to implement the embodiments of the disclosure may be implemented as part of an operating system or a specific application, component, program, object, module, or sequence of instructions (collectively referred to as "computer programs"). The computer programs typically comprise one or more instructions (e.g., instructions 1404, 1408, 1428) set at various times in various memory and storage devices in a computing device. When read and executed by the processor 1402, the instructions cause the processing system 1400 to perform operations to execute elements involving the various aspects of the present disclosure.

Further examples of machine- and computer-readable media include recordable-type media, such as volatile memory devices and non-volatile memory devices 1410, removable disks, hard disk drives, and optical disks (e.g., Compact Disk Read-Only Memory (CD-ROMS) and Digital Versatile Disks (DVDs)), and transmission-type media, such as digital and analog communication links.

The network adapter 1412 enables the processing system 1400 to mediate data in a network 1414 with an entity that is external to the processing system 1400 through any communication protocol supported by the processing system 1400 and the external entity. The network adapter 1412 can include a network adaptor card, a wireless network interface card, a router, an access point, a wireless router, a switch, a multilayer switch, a protocol converter, a gateway, a bridge, bridge router, a hub, a digital media receiver, a repeater, or any combination thereof.

Remarks

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling those skilled in the relevant art to understand the claimed subject matter, the various embodiments, and the various modifications that are suited to the particular uses contemplated.

Although the Detailed Description describes certain embodiments and the best mode contemplated, the technology can be practiced in many ways no matter how detailed the Detailed Description appears. Embodiments may vary considerably in their implementation details, while still being encompassed by the specification. Particular terminology used when describing certain features or aspects of various embodiments should not be taken to imply that the terminology is being redefined herein to be restricted to any specific characteristics, features, or aspects of the technology with which that terminology is associated. In general, the terms used in the following claims should not be construed to limit the technology to the specific embodiments disclosed in the specification, unless those terms are explicitly defined herein. Accordingly, the actual scope of the technology encompasses not only the disclosed embodiments, but also all equivalent ways of practicing or implementing the embodiments.

The language used in the specification has been principally selected for readability and instructional purposes. It may not have been selected to delineate or circumscribe the subject matter. It is therefore intended that the scope of the technology be limited not by this Detailed Description, but rather by any claims that issue on an application based hereon. Accordingly, the disclosure of various embodiments is intended to be illustrative, but not limiting, of the scope of the technology as set forth in the following claims.

What is claimed is:

1. An apparatus for generating computer vision data, the apparatus comprising:
   a camera configured to generate digital images of an environment in which an individual is situated over an interval of time;
   a processor configured to:
      generate computer vision data via an analysis of the digital images with a neural network,
         wherein the neural network outputs, for each of the digital images, a pose of the individual so as to establish serialized poses of the individual over the interval of time, and
      encode the computer vision data into a portable data structure; and
   a communication module configured to communicate the digital images and the portable data structure to a second apparatus with a graphics processing unit, at which the digital images are stored and the portable data structure is decoded for analysis of the computer vision data and determination of a health status of the individual.

2. The apparatus of claim 1, wherein the second apparatus is able to display the computer vision data, or analyses of the computer vision data, so as to visually indicate the health status of the individual.

3. The apparatus of claim 1, wherein the health status is representative of a musculoskeletal health state.

4. The apparatus of claim 1, wherein the computer vision data indicates, for each of the digital images, two-dimensional locations of one or more joints of the individual.

5. The apparatus of claim 1, wherein the computer vision data indicates, for each of the digital images, three-dimensional locations of one or more joints of the individual.

6. The apparatus of claim 1, wherein the computer vision data indicates, for each of the digital images, three-dimensional rotation of one or more joints of the individual.

7. The apparatus of claim 1, wherein the computer vision data indicates, for each of the digital images, a location, a size, and/or a shape of one or more muscles of the individual.

8. The apparatus of claim 1, wherein the computer vision data includes a thermal map that is representative of a surface of a body of the individual.

9. The apparatus of claim 1, wherein the computer vision data includes a volumetric representation of the individual that is comprised of voxels, each voxel representing a location whose spatial position is determined by the neural network.

10. A method for determining, with a first computing device with a graphics processing unit, a health status of an individual through analysis of computer vision data generated by a second computing device with a central processing unit, the method comprising:
   acquiring, by the second computing device, a series of digital images generated by a camera in rapid succession of an environment in which an individual is situated;
   applying, by the second computing device, a model to the series of digital images to produce a series of outputs, wherein each output in the series of outputs is representative of information regarding a spatial position of the individual as determined through analysis of a corresponding digital image of the series of digital images, and
   wherein the series of outputs are collectively representative of computer vision data;
   populating, by the second computing device, the series of outputs into a data structure that is transmitted to the first computing device;
   assessing, by the first computing device based on the computer vision data in the data structure, health of the individual in real time; and
   performing, by the first computing device, an action based on the health of the individual.

11. The method of claim 10, wherein said assessing comprises determining musculoskeletal performance of the individual, and wherein the method further comprises:
   receiving, by either the first computing device or the second computing device, input indicative of a request to initiate an exercise therapy session; and
   causing, by either the first computing device or the second computing device, presentation of an instruction to the individual to perform an exercise;
   wherein the series of digital images are generated by the camera as the individual performs the exercise.

12. The method of claim 11, wherein in response to a determination that the individual completed the exercise, said performing comprises instructing the individual to perform another exercise.

13. The method of claim 10, wherein said assessing comprises performing fall detection based on the computer vision data.

14. The method of claim 10, wherein said assessing comprises performing gait analysis based on the computer vision data.

15. The method of claim 10, wherein said assessing comprises performing activity analysis based on the computer vision data, the activity analysis indicating an estimated level of effort being employed by the individual.

16. The method of claim 10, wherein said assessing comprises performing fine motor skill analysis based on the computer vision data.

17. The method of claim 10, wherein said assessing comprises performing range of motion analysis based on the computer vision data.

18. The method of claim 10, wherein said assessing comprises performing muscle fatigue analysis based on the computer vision data, the muscle fatigue analysis indicating an estimated level of fatigue being experienced by a muscle of the individual.

19. The method of claim 10, wherein said assessing comprises performing muscle distribution analysis based on the computer vision data, the muscle distribution analysis indicating an estimated location, size, and/or shape of a muscle of the individual.

20. The method of claim 10, wherein said assessing comprises performing body mass index (BMI) analysis based on the computer vision data.

21. The method of claim 10, wherein said assessing comprises performing blood flow analysis based on the computer vision data, the blood flow analysis indicating whether an estimated speed and/or volume of blood flow through the individual is abnormal.

22. The method of claim 10, wherein said assessing comprises performing temperature analysis based on the computer vision data, the temperature analysis indicating temperature along a surface of a body of the individual in at least two different locations.

23. The method of claim 10, further comprising:
   providing, by the second computing device, the series of digital images to an encoder that produces, as output, an encoded data structure that is transmitted to the first computing device.

24. The method of claim 10, wherein the series of outputs are encoded into data structure by the second computing device, and wherein the method further comprises:
providing, by the first computing device, the encoded data structure to a decoder that produces, as output, a decoded data structure from which the series of outputs can be extracted for analysis.

25. A system for assessing health of an individual, the system comprising:
a plurality of imaging apparatuses that are deployed in an environment in which an individual is situated, wherein each imaging apparatus comprises:
an image sensor configured to produce digital images of the individual over an interval of time,
a central processing unit configured to:
generate a dataset that is representative of information related to the individual that is learned through analysis of the digital images, and
populate the dataset into a data structure, and
a communications interface via which the data structure exits the imaging apparatus; and
a processing apparatus that comprises:
a decoder,
a communications interface at which to receive a plurality of data structures from the plurality of imaging apparatuses, and
a graphics processing unit configured to:
provide the plurality of data structures to the decoder, so as to obtain a plurality of datasets, each of which corresponds to a different one of the plurality of data structures, and
assess health of the individual by examining the plurality of datasets that are output by the decoder for the plurality of data structures.

26. The system of claim 25, wherein the image sensor included in each imaging apparatus is designed to cover the infrared, near infrared, visible, or ultraviolet regions.

27. The system of claim 25, wherein the communications interface of the processing apparatus is part of a transceiver configured to facilitate wireless communication with each imaging apparatus via a separate communication channel.

28. The system of claim 25, wherein the central processing unit of each imaging apparatus is further configured to append metadata that identifies the imaging apparatus to the data structure.

29. The system of claim 25, wherein the plurality of imaging apparatuses are deployed in the environment such that each imaging apparatus produces the digital images of the individual from a different perspective.

30. The system of claim 25, wherein the central processing unit of each imaging apparatus generates the dataset by applying one or more computer vision algorithms to the digital images.

31. The system of claim 25, wherein at least one of the plurality of imaging apparatuses and the processing apparatus are representative of a single computing device.

32. The system of claim 25, wherein the information specifies two- or three-dimensional locations of at least two joints of the individual over the interval of time.

* * * * *